United States Patent [19]

Ashton et al.

[11] Patent Number: 4,880,820
[45] Date of Patent: Nov. 14, 1989

[54] GUANINE DERIVATIVES

[75] Inventors: Wallace T. Ashton; Laura F. Canning, both of Clark, N.J.; Arthur K. Field, North Wales, Pa.; Richard L. Tolman, Warren, N.J.

[73] Assignee: Merck & Co., Inc., Rahway, N.J.

[21] Appl. No.: 150,478

[22] Filed: Feb. 8, 1988

Related U.S. Application Data

[63] Continuation of Ser. No. 616,910, Jun. 6, 1984, abandoned, which is a continuation-in-part of Ser. No. 507,328, Jun. 24, 1983, abandoned.

[51] Int. Cl.$^4$ .................... C07D 473/18; A61K 31/52
[52] U.S. Cl. .................... 514/322; 544/276; 544/277; 546/199
[58] Field of Search ................ 546/199; 544/276, 277; 514/322

[56] References Cited

U.S. PATENT DOCUMENTS

| | | | |
|---|---|---|---|
| 4,027,025 | 5/1977 | Schaeffer | 424/200 |
| 4,146,715 | 3/1979 | Schaeffer | 544/276 |
| 4,199,574 | 4/1981 | Schaeffer | 424/200 |
| 4,294,831 | 10/1981 | Schaeffer | 424/253 |
| 4,347,360 | 8/1982 | Ogilvie | 544/276 |
| 4,355,032 | 10/1982 | Verheyden et al. | 424/253 |
| 4,556,659 | 12/1987 | Verheyden et al. | 544/276 |
| 4,565,868 | 1/1986 | Verheyden et al. | 544/276 |

FOREIGN PATENT DOCUMENTS

| | | |
|---|---|---|
| 0049072 | 4/1982 | European Pat. Off. . |
| 0074306 | 3/1983 | European Pat. Off. . |
| 0085424 | 8/1983 | European Pat. Off. . |
| 0095813 | 12/1983 | European Pat. Off. . |
| 0105486 | 4/1984 | European Pat. Off. . |
| 1523865 | 9/1978 | United Kingdom . |
| 1567671 | 5/1980 | United Kingdom . |
| 1590500 | 6/1981 | United Kingdom . |

OTHER PUBLICATIONS

De Clerc, G., Jour. of Med. Chem., pp. 510–513 (1978).
Jour. of Med. Chem., vol. 14, No. 4 (1971), pp. 367, 368, 369.
Keller et al, Biochem. Pharm., vol. 30, No. 22 (1981), 3071–3077.
Smith et al, Antimicrobial Agents & Chemotherapy, vol. 22, No. 1 (1982), pp. 55–61.
Ogilvie et al, Tetrahedron Letters, vol. 21 (1980), pp. 327–330.
Chemical Abstracts, vol. 97, No. 15 (1982), No. 120161c.
Gillen, Thesis, Synthesis & Properties of Novel Nucleosides & Nucleoside Analogues (1980).
A. Larsson et al., Antimicrobial Agents and Chemotherapy, vol. 23, 664–670 (1983).
Lin et al., Tetrahedron Letters, vol. 25, 905–906 (1984).
Colla et al., J. Med. Chem., 26, 602–604 (1983).

*Primary Examiner*—Nicholas S. Rizzo
*Attorney, Agent, or Firm*—Richard S. Parr; Michael C. Sudol

[57] ABSTRACT

(S)-9-(2,3-dihydroxy-1-propoxymethyl)guanine has potent antiherpetic activity which is superior to the corresponding racemic mixture or the (R)-enantiomer and also is much more potent than 9-(2-hydroxyethoxymethyl)guanine. Acyl derivatives (prodrugs) of the (S)-enantiomer, which are more effective than the corresponding (R)-enantiomer analogs or related racemic mixtures provide formulation advantages and even higher plasma half lives in animals or man than the (S)-isomer.

12 Claims, No Drawings

GUANINE DERIVATIVES

This is a continuation of application Ser. No. 616,910, filed June 6, 1984, now abandoned, which is a continuation-in-part of Ser. No. 507,328, filed June 24, 1983, now abandoned.

BACKGROUND OF THE INVENTION (S)-9-(2,3-dihydroxy-1-propoxymethyl)guanine has been found to possess substantial antiviral activity against various herpes viruses. This compound has significantly greater antiviral activity against herpes viruses than antiherpetic agents currently in use such as 9-(2-hydroxyethoxymethyl)guanine (acyclovir).

SUMMARY OF THE INVENTION

It has now been found that (S)-9-(2,3-dihydroxy-1-propoxymethyl)guanine has potent antiherpetic activity which is better than the corresponding racemic mixture or the (R)-enantiomer and which also is much more potent than the commercially marketed product 9-(2-hydroxyethoxymethyl)guanine. The acyl derivatives of the (S)-enantiomer are also more effective than those of the corresponding racemic mixtures or (R)-enantiomers. A synthesis of the foregoing (S)-enantiomer from chiral intermediates is provided. Also provided are syntheses of corresponding mono- and di-O-acyl derivatives which have formulation advantages and are prodrugs providing even higher and/or longer plasma half lives in animals and man than the (S)-isomer.

DETAILED DESCRIPTION

The present invention relates to (S)-9-(2,3-dihydroxy-1-propoxymethyl)guanine and its acyl derivatives which are potent antiherpetic agents. These compounds may be represented as compounds of the formula:

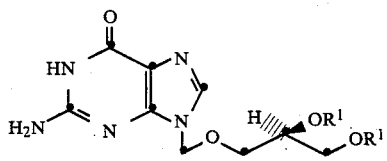

I wherein each $R^1$ is independently H or

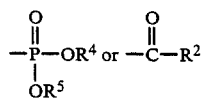

wherein each $R^2$ is independently alkyl of 1 to 20 carbon atoms (preferably alkyl of 1 to 10 carbon atoms) which may be straight chain or branched, saturated or mono- or polyunsaturated, and may contain one or more hydroxy, amino or carboxyl groups, phenyl, phenyl substituted with halogen (i.e., fluorine, chlorine, bromine or iodine), phenyl substituted with alkyl of 1 to 4 carbon atoms, pyridyl, piperidyl, furyl, imidazolyl, tetrahydrofuryl, thienyl, phenylalkyl wherein the alkyl moiety has 1 to 4 carbon atoms, alkoxyalkyl wherein both the alkoxy and alkyl moieties contain 1 to 4 carbon atoms, or phenoxy substituted with alkyl having 1 to 4 carbon atoms, or the two $R^1$ groups together are

and wherein $R^4$ and $R^5$ are independently H; a pharmaceutically acceptable cation (for example, sodium, potassium, ammonium, $C_1$ to $C_4$ alkyl substituted ammonium, magnesium/2, calcium/2, or aluminum/3), straight or branched chain alkyl of 1 to 8 carbon atoms, phenyl, phenyl substituted by halogen, phenyl substituted by alkyl of 1 to 4 carbon atoms, phenylalkyl wherein the alkyl moiety has 1 to 4 carbon atoms, phosphate or pyrophosphate.

The following are examples of suitable $R^2$ groups: $-CH(CH_3)NH_2$, $-CH_2NH_2$, $-CH(CH_2OH)NH_2$, $-(CH_2)_2COOH$, $-CH_2OH$, $-CH(NH_2)CH_2COOH$.

The present invention also relates to a synthesis for the preparation of the foregoing (S)-enantiomers from chiral intermediates. (S)-9-(2,3-dihydroxy-1-propoxymethyl)guanine may be prepared starting from 2,3-di-O-benzyl-L-glycerol [Wickberg, Acta Chem. Scand., 12, 1187 (1958)] and treating the latter with paraformaldehyde and anhydrous HCl preferably near 0° C. to form the corresponding chloromethyl ether. The chloromethyl ether can then be reacted with tris(trimethylsilyl)guanine at temperatures generally above 100° C., preferably in an inert solvent such as xylene. Desilylation, for example with hot n-propanol, yields the compound of Formula I where $R^1$ is benzyl. Debenzylation of the compound of Formula I where $R^1$ is benzyl by catalytic hydrogenolysis (palladium hydroxide on carbon is a preferred catalyst) in the presence of 2 equivalents of a strong acid such as p-toluenesulfonic acid, and preferably in an alcoholic solvent, yields (S)-9-(2,3-dihydroxy-1propoxymethyl)guanine which may be represented as follows:

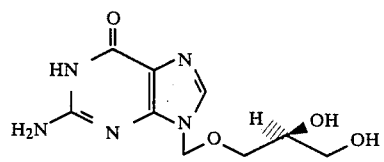

II

Debenzylation also may be accomplished by other compatible methods known in the literature, such as transfer hydrogenation in the presence of a palladium catalyst in a mixture of cyclohexene and alcohol as described, for example, by Ogilvie et al., Can. J. Chem. 60, 3005 (1982) or Martin et al., J. Med. Chem., 26, 759 (1983), or by reduction with sodium in liquid ammonia as described, for example, by Ogilvie, vide supra.

Phosphorylation of the compound of Formula II can be accomplished by treatment with any of many well-known phosphorylating agents in an inert aprotic solvent. Preferred phosphorylating agents are phosphoryl chloride in triethyl phosphate and diphenylphosphorochloridate in acetonitrile. Phosphotriester protecting groups are removed by hydrogenolysis and/or saponification.

Useful acyl derivatives of the compound of Formula II are prepared by acylation with any of a variety of acylating agents such as acyl halides, activated acyl esters (for example, p-nitrophenyl), acid anhydrides, or by the desired acid in the presence of an activating agent such as N,N'-dicyclohexylcarbodiimide or diethyl azodicarboxylate/triphenylphosphine. The reactions are usually performed at ice temperature to ambient temperature in polar aprotic solvents, preferably dimethylformamide or pyridine, but with less reactive acylating agents temperatures up to 100° may be required. Yields are improved by the use of mixed solvents, dimethylformamide-pyridine being one of the most useful. Triethylamine can be added as an acid acceptor and facilitates the reaction with acid anhydrides, particularly succinic anhydride. When the acyl group contains a hydrophilic group such as amino, hydroxy or carboxyl, the group must be protected during the acylation reaction preferably as the carbobenzyloxy derivative (in the case of amino), or as the benzyl ether (in the case of hydroxy), or as the benzyl ester or internal anhydride (in the case of carboxyl). The protecting groups are all removed by standard hydrogenation conditions known to those skilled in the art.

Thus, the present invention also relates to chemical intermediates for compounds of the formula I, said intermediates being compounds of the formula

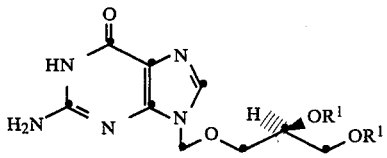

I wherein each $R^1$ is independently H or benzyl or

wherein each $R^2$ is independently alkyl of 1 to 20 carbon atoms which may be straight chain or branched, saturated or mono- or polyunsaturated, and may contain one or more hydroxy, amino or carboxyl groups, with the proviso that if $R^1$ is H or

then a hydrogen on each hydroxy and carboxy group of $R^2$ is replaced by a benzyl group and a hydrogen of each amino group of $R^2$ is replaced with a carbobenzyloxy group.

The compounds of the present invention may be employed as an anti-viral compounds in mammalian or avian or piscine species in dosage levels effective to impart an anti-herpes virus activity. Typically such levels are from about 1 to about 200 mg/kg/day. The compounds may also be effective against other viruses. The compounds of the present invention may be formulated accordingly to accepted pharmaceutical practice for administration orally, topically or by injection. Suitable oral dosage forms are tablets, capsules, elixirs or powders, while solutions or suspensions in, for example, phosphate buffered saline or water are suitable for injection. Examples of suitable topical formulations are gels, ointments, solutions or suspensions.

EXAMPLE 1

Synthesis of (S)-9-(2,3-dihydroxy-1-propoxymethyl) guanine

A mixture of 54.4 g (200 mmole) of 2,3-di-O-benzyl-L-glycerol, 6.00 g (200 mmole) of paraformaldehyde, and 200 ml of methylene chloride was stirred vigorously as HCl gas was bubbled in rapidly for 5 minutes and then at a slower rate. After 4 hours the mixture was removed from the ice bath, treated with anhydrous $Na_2SO_4$, and filtered. Concentration of the filtrate under reduced pressure (less than or equal to 100 mm) with mild warming followed by drying under high vacuum gave 61.5 g (96%) of chloromethyl 2,3-di-O-benzyl-L-glyceryl ether as a light yellow oil (purity greater than 93% by NMR in $CDCl_3$).

A mixture of 20.5 g (135 mmole) of guanine, 135 ml of bis(trimethylsilyl)acetamide, 2.0 ml of trimethylsilyl chloride, and 0.45 ml of triethylamine was stirred under $N_2$ in an oil bath at +115° C. After 6 hours the resulting solution was cooled and concentrated under reduced pressure (high vacuum 0.3 mm, bath temperature raised to 90° C.) until no more bubbling was observed. The viscous, amber residual oil was removed under $N_2$, immediately covered with 150 ml of xylene, and stoppered.

This solution of tris(trimethylsilyl)guanine (135 mmole) in 150 ml of xylene was stirred under $N_2$ in an oil bath at about 115° C. as a solution of 53.5 g (155 mmole based on purity of 93%) of chloromethyl 2,3-di-O-benzyl-L-glyceryl ether in 50 ml of xylene was added dropwise over 30 minutes. The oil bath was then raised to 125° C. and maintained at this temperature for 12 hours. The cooled solution was concentrated under high vacuum. The viscous residual oil was covered with 300 ml of n-propanol, and the mixture was stirred under reflux. A clear solution was obtained, but precipitation began within a few minutes. After 1 hour the mixture was cooled. The precipitated solid was collected on a filter and washed successively with n-propanol, a small volume of acetone, more n-propanol, and finally ether. Recrystallization from n-propanol-acetic acid yielded, after washing with ether and air drying, 29.4 g (50%) of 9-(2,3-di-O-benzyl-L-glycer-1-yloxymethyl)guanine as light yellow crystals, m.p. 198.5–200.5° C. Structure and purity were confirmed by NMR (DMSO-$d_6$) and TLC (9:1 $CHCl_3$-MeOH).

A mixture of 15.22 g (35 mmole) of the foregoing compound, 13.30 g (70 mmole) of p-toluenesulfonic acid monohydrate, 3.75 g of 20% palladium hydroxide on carbon, and 150 ml of methanol was shaken with hydrogen (initial pressure 46 psig) on a Parr apparatus. After 23 hours, by which time TLC indicated complete reaction, the mixture was diluted with 75 ml of $H_2O$ and titrated to approximately pH7 with 2.5 N NaOH (about 28 ml). The mixture was then concentrated to small volume under reduced pressure (less than or equal to 100 mm). Water was added back to the concentrate to give a total volume of about 110 ml. The mixture was heated to boiling and filtered through Solka-Floc to remove the catalyst. The filter cake was washed with some additional boiling $H_2O$. After reheating, the filtrate was allowed to cool slowly. The crystallized product was collected on a filter and washed with some cold $H_2O$, then with ether and acetone. The material was recrystallized from $H_2O$, and the product was dried in a vacuum oven (less than or equal to 100 mm) at room temperature to give 4.64 g (49%) of (S)-9(2,3-dihydroxy-1-propoxymethyl)guanine monohydrate as white crystals, m.p. 244°–245° C. (partial decomposition). The material was homogeneous by TLC (80:20:2 $CHCl_3$-MeOH-$H_2O$), and reverse phase analytical HPLC (Whatman ODS-3, in $H_2O$), and 200 MHz NMR (DMSO-$d_6$).

NMR (DMSO-$d_6$)δ: 3.25–3.6 (m, 5H, $CH_2CHCH_2$), 4.55 (t, J=6Hz, 1H, $CH_2OH$), 4.77 (d, J=5Hz, 1H, CHOH), 5.37 (s, 2H, $NCH_2O$), 6.55 (br s, 2H, $NH_2$), 7.85 (s, 1H, C8H), 10.58 (br s, 1H, $N^1H$).

UV: λmax (pH 1) 255 nm (ϵ13,600), 275 nm (shoulder, ϵ9,170); λmax (pH 7) 251 nm (ϵ13,800), 268 nm (shoulder, ϵ9,660); λmax (pH 13) 264 nm (ϵ11,000) confirmed the assigned structure.

The following optical rotations were obtained: $[α]_D^{20} = +1.5°$, $[α]_{436}^{20} = +3.1°$, $[α]_{365}^{20} = +4.8°$ (c=2.0, 0.1 N NaOH).

Anal. ($C_9H_{13}N_5O_4 \cdot H_2O$)
Calcd.: C, 39.56; H, 5.53; N, 25.63.
Found: C, 39.22; H, 5.41; N, 25.47.

EXAMPLE 2

(S)-9-(2,3-Diacetoxy-1-propoxymethyl)guanine

A mixture of 5.34 g (20 mmole) of hydrated (S)-9-(2,3-dihydroxy-1-propoxymethyl)guanine, 40 ml of acetic anhydride (increased to 100 ml after several days), 40 ml of pyridine (increased to 80 ml after a few days) and 160 ml of dimethylformamide is stirred at room temperature under a drying tube for a total of 20 days and then concentrated in vacuo. The residue is triturated with 30 ml of methylene chloride and diluted with 100 ml of ether. The solid is collected on a filter, washed with ether, and recrystallized from dioxane-acetic acid to give the title compound.

EXAMPLE 3

(S)-9-(2,3-Dipropionyloxy-1-propoxymethyl)guanine

A mixture of 205 mg (0.75 mmole) of (S)-9-(2,3-dihydroxy-1-propoxymethyl)guanine monohydrate, 1.5 ml of propionic anhydride, 6 ml of dry dimethylformamide, and 1.5 ml of dry pyridine is stirred at room temperature under a drying tube. After 4 days the mixture is diluted with 25 ml of ether. The solid is collected on a filter and washed with ether. It is recrystallized from isopropanol.

EXAMPLE 4

(S)-9-(2-Hydroxy-3-octanoyloxy-1-propoxymethyl)guanine

A suspension of 410 mg (1.5 mmole) of (S)-9-(2,3-dihydroxy-1-propoxymethyl)guanine monohydrate in 6 ml of dry dimethylformamide and 1.5 ml of dry pyridine is stirred under a drying tube with cooling in an ice bath as a solution of 489 mg (3.0 mmole) of octanoyl chloride in 1.5 ml of dimethylformamide is added dropwise by syringe over approximately 5 minutes. The mixture is allowed to warm gradually to room temperature, and after 24 hours it is concentrated under high vacuum. The residual oil is purified by preparative TLC on nine 1000-μ silica gel plates (developed in 5:1 $CHCl_3$-MeOH). The product bands are isolated, combined, and extracted with dimethylformamide.

EXAMPLE 5

(S)-9-(2,3-Dioctanoyloxy-1-propoxymethyl)guanine

A suspension of 267 mg (1 mmole) of hydrated (S)-9-(2,3-dihydroxy-1-propoxymethyl)guanine in 4 ml of dry dimethylformamide and 1.4 ml of dry pyridine is stirred under nitrogen at 0° C. as 0.68 ml (650 mg, 4 mmole) of octanoyl chloride in 1.6 ml of dimethylformamide is added dropwise. The mixture is allowed to warm gradually to room temperature. After stirring overnight, it is concentrated in vacuo. The residue is chromatographed on a silica gel column (gradient elution with methylene chloride containing 0–5% methanol) to give a solid, which is triturated and washed with chloroform and ether to obtain the title compound.

EXAMPLE 6

(S)-9-(2,3-Dibenzoyloxy-1-propoxymethyl)guanine

A suspension of hydrated (S)-9-(2,3-dihydroxy-1-propoxymethyl)guanine (1 mmole) in 4 ml of dry dimethylformamide and 1.4 ml of dry pyridine is stirred under nitrogen in an ice bath as a solution of benzoyl chloride (4 mmole) in 1.6 ml of dimethylformamide is added dropwise. The mixture is allowed to warm gradually to room temperature. After stirring overnight, the solution is concentrated under high vacuum. The residue is chromatographed on silica gel (elution with $CH_2Cl_2$-MeOH). Trituration of the residue with ether and then with chloroform gives the title compound.

EXAMPLE 7

(S)-9-[2,3-Bis(phenoxyacetoxy)-1-propoxymethyl]guanine

A suspension of 267 mg (1 mmole) of hydrated (S)-9-(2,3-dihydroxy-1-propoxymethyl)guanine in 4 ml of dry dimethylformamide and 1.4 ml of dry pyridine is stirred under nitrogen in an ice bath as a solution of 0.55 ml (682 mg, 4 mmole) of phenoxyacetyl chloride in 1.6 ml of dimethylformamide is added dropwise. After gradually warming to room temperature, the mixture is stirred overnight and then evaporated under vacuum. Chromatography of the residue on silica gel (elution with methylene chloride-methanol) gives a solid, which is recrystallized from isopropanol, to give the title compound.

EXAMPLE 8

(S)-9-[2,3-bis(azidoacetoxy)-1-propoxymethyl]guanine

A solution of 0.84 ml (8.4 mmol) of azidoacetyl chloride in 5 ml of dimethylformamide is added dropwise over a period of 10 minutes to an ice-cooled stirred suspension of 0.66 g (2.5 mmol) of (S)-9-(2,3-dihydroxy-1-propoxymethyl)guanine monohydrate and 1.05 ml (7.5 mmol) of triethylamine in dry dimethylformamide (40 ml). After stirring for 45 minutes at 0°, the reaction is allowed to warm to ambient temperature for 30 minutes and is quenched with 7% sodium bicarbonate solution (15 ml). The mixture is evaporated to dryness in vacuo and the residue is extracted with dichloromethane (3×50 ml). The organic extract is washed with cold water, dried, and evaporated to a residue which is recrystallized from a suitable solvent such as aqueous methanol to furnish the pure product.

EXAMPLE 9

(S)-9-[2,3-Bis(N-carbobenzyloxyglycyloxy)-1-propoxymethyl]guanine

To a solution of 1.65 g of N-carbobenzyloxyglycine in 4 ml of dry dimethylformamide is added 1.48 g of N,N'-dicyclohexylcarbodiimide, and stirring is continued at room temperature for 1 hour, during which time N,N'-dicyclohexylurea precipitates. The reaction mixture is then filtered directly into another flask containing a suspension of (S)-9-(2,3-dihydroxy-1-propoxymethyl)guanine in 4 ml of dry dimethylformamide (largely in solution after mild warming). The resulting mixture is treated with a few crystals of 4-dimethylaminopyridine and then stirred under nitrogen at room temperature for 21 hours. The mixture is filtered, and the filtrate is concentrated in vacuo. The gelatinous residue is seeded with crystals obtained by trituration with acetonitrile. Crystallization occurs on prolonged standing. This material is isolated and dissolved in tetrahydrofuran-water (60:40) and evaporated onto silica gel, which is then eluted with 80:20:2 chloroform-methanol-water. Fractions containing pure diacylated product by TLC are combined to give the title compound.

EXAMPLE 10

(S)-9-(2,3-Diglycyloxy-1-propoxymethyl)guanine

Method 1:

The product from Example 8 (1.23 g) is hydrogenated (H2 pressure =40 psi) in 50% aqueous ethanol in the presence of 10% of Pd/C (1.0 g) and 1.0 N HCl (4 ml). After the reaction is shown to be complete by TLC (about 1.5 hours), the catalyst is filtered and washed well with water. The volume is reduced in vacuo in order to cause the product to crystallize. Filtration and recrystallization from aqueous ethanol gives the title compound.

Method 2:

This material is prepared by hydrogenation of (S)-9-[2,3-bis(N-carbobenzyloxyglycyloxy)-1-propoxymethyl]guanine as described for the synthesis of (S)-9-(2,3-dialanyloxy-1-propoxymethyl)guanine (Example 11).

EXAMPLE 11

(S)-9-(2,3-Dialanyloxy-1-propoxymethyl)guanine

A mixture of 0.54 g (2 mmol) of (S)=-9(2,3-dihydroxy-1-propoxymethyl)guanine, 1.026 g (4.3 mmol) of N-carbobenzyloxy-DL-alanine, 0.04 g anhydrous p-toluenesulfonic acid, and 1.755 g (5.6 mmol) of N,N'-dicyclohexylcarbodiimide in dry pyridine (80 ml) is stirred for 24 hours. Acetic acid (1 ml) is added and the mixture is stirred for an additional hour. The reaction mixture is filtered and the residue is washed with methanol. The filtrate is evaporated to dryness in vacuo and chromatographed on silica gel ($CH_2Cl_2$/MeOH, 9:1). Evaporation of the product-containing fractions and recrystallization from aqueous ethanol gives the protected ester. Removal of the CBZ group is accomplished by hydrogenation in 50% aqueous methanol (300 ml/1.0 g protected ester) containing two equivalents of HCl as a 0.5 N solution using 10% Pd/C (0.5 g/1.0 g protected ester) at 40 psi of hydrogen for 2 hours. The catalyst is filtered, washed with water and the filtrate is evaporated to dryness in vacuo. Recrystallization from aqueous ethanol furnishes the title compound.

EXAMPLE 12

(S)-9-[2,3-Bis(3-carboxypropyloxy)-1-propoxymethyl]guanine

A solution of (S)-9-(2,3-dihydroxy-1propoxymethyl)guanine (1.37 g, 5 mmol), 2.0 g of succinic anhydride, and 2.8 ml of anhydrous triethylamine in dry dimethylformamide (75 ml) is heated in an oil bath at 60°. When the reaction is complete (24 hours) the mixture is cooled and evaporated to dryness in vacuo. The residue is resuspended in ice-water (50 ml) and the pH is adjusted to 2 with 2N-HCl. The precipitate is filtered, thoroughly washed with ice-water, and dried in vacuo. The precipitate is then recrystallized from methanol.

EXAMPLE 13

(S)-9-(2,3-dihydroxy-1-propoxymethyl)guanine cyclic carbonate, alternatively named as (S)-9-(2-oxo-1,3-dioxolan-4-yl-methoxymethyl)guanine A solution of 267 mg (1 mmole) of hydrated (S)-9-(2,3-dihydroxy-1-propoxymethyl)guanine in 10 ml of dry dimethylformamide is stirred at 80° C. as 300 mg (1.85 mmole) of N,N'-carbonyldiimidazole is added gradually over 6 hours. After stirring overnight at this temperature, the solution is concentrated to dryness. The residual solid is triturated with water, collected on a filter, and washed with acetone. The material may be recrystallized from 2-methoxyethanol-water.

EXAMPLE 14

In vitro Assays:

Method 1: Confluent monolayers of primary rabbit kidney cell cultures were refed with maintenance medium containing serial dilutions of the test compounds and incubated overnight at 37° C. At each dilution, four cultures were challenged with approximately 10 TCID50 HSV-1, four cultures were challenged with approximately 10 TCID50 HSV-2, and two cultures were left as toxicity controls. Cultures were reincubated at 37° C. and observed for viral induced cytopathology at days 5 and 7. Minimum Effective Concentration ($\mu$g/ml) is defined as the concentration of antiviral compound required to totally suppress the development of viral cytopathology in 50% of the infected rabbit kidney cell cultures. The following antiviral compounds were tested:

A. (S)-9-(2,3-dihydroxy-1-propoxymethyl)guanine
B. (R)-9-(2,3-dihydroxy-1-propoxymethyl)guanine
C. Racemic 9-(2,3-dihydroxy-1-propoxymethyl)guanine

| | Results: | | |
|---|---|---|---|
| | Minimum Effective Concentration ($\mu$g/ml) | | |
| Virus | A | B | C |
| Herpes simplex virus Type 1 (Schooler) | 0.8–1.5 | 25 | 3.1–6 |
| Herpes simplex virus Type 2 (Curtis) | 3.1 | 25–50 | 6–12 |

In vitro assays:

Method 2: Confluent monolayers of MRC-5 cells were incubated for one hour at 37° C. with 50–100 plaque forming units of the indicated virus. Following incubation, the cell monolayers were refed with maintenance medium containing 2% methyl cellulose and the chemical agent indicated. Duplicate cultures were incubated with each concentration of the chemical agent tested. Following further incubation for 3 days at 37° C., the monolayers were stained and the developed virus plaques were counted. The concentration ($\mu$g/ml) of each chemical agent which reduced plaque development by 50% (ED$_{50}$) was determined.

| | ED$_{50}$ ($\mu$g/ml) | | |
|---|---|---|---|
| Virus | A | B | C |
| Herpes simplex virus | 0.5 | 6.2 | 1.0 |

-continued

| Virus | ED$_{50}$ (μg/ml) | | |
|---|---|---|---|
| | A | B | C |
| Type 1 (Schooler) | | | |

Conclusion

A was 10 to 25-fold more effective than B and about 2-fold more active than C in protecting cell cultures against HSV-1 infection.

EXAMPLE 15

Parenteral Treatment of Herpes Simplex Virus Infection in Mice

Twenty gram ICR/Ha mice were injected intraperitoneally (ip) with 0.5 ml of a $10^{-5}$ dilution of a stock preparation of Herpes simplex virus type 1 (HSV-1), strain Schooler. This virus challenge infected each animal with approximately 50 to 100 LD50. Starting immediately after virus infection and continuing twice daily for 4 days, each animal was injected subcutaneously in groups of 10 with: 125 μg, 31 μg, 8 μg or 2 μg of compounds A, B or C; or placebo (physiological saline, pH 11.5). All compounds were solubilized in physiological saline, pH 11.5. The mice were observed daily for 15 days at the same time each day and the day of death was recorded for each animal.

Statistical analyses [reference: Liddel, F.D.K., Evaluation of Survival in Challenge Experiments, Microbiol. Rev., 42, 237 (1978)] were performed on survival times transformed by the negative exponential transformation:

$$f(t) = 1 - (0.1)^{t/T}$$

where
t = number of days an animal survived
T = duration of trial (15 days)

A continuity correction was used to account for daily observation:

$$f_c(t) = \tfrac{1}{2}[f(t) + f(t-1)]$$

Within each group, mice surviving through the trial period were assigned equally values of 0.9 and 1.0 to adjust for termination of the trial.

Average survival time per group was calculated from average corrected transformed survival times [$f_c(t)$] as follows:

$$t\,avg = [T/log(0.1)] \cdot [log(1 - f_c(t)]$$

The summarized results are shown in the following table:

| Treatment of Herpes Simplex Virus Infection in Mice | | | | |
|---|---|---|---|---|
| Chemical Agent | Animal Treatment | | Percent Survival[1] | Avg. Survival Time (Days) |
| | μg/dose | mg/kg/day | | |
| A. | 125 | 12.5 | 40 | 10.7 |
| | 31 | 3.1 | 10 | 7.6[3] |
| | 8 | 0.8 | 0 | 6.7[3] |
| | 2 | 0.2 | 0 | 6.1[3] |
| B. | 125 | 12.5 | 10 | 7.5[3] |
| | 31 | 3.1 | 10 | 6.5[3] |
| | 8 | 0.8 | 0 | 6.3[3] |
| | 2 | 0.2 | 0 | 6.0[3] |
| C. | 125 | 12.5 | 20 | 8.6 |
| | 31 | 3.1 | 0 | 7.2[3] |
| | 8 | 0.8 | 0 | 6.6[3] |
| | 2 | 0.2 | 10 | 6.7[3] |
| Acyclovir[2] | 1000 | 100 | 10 | 7.8 |
| | 500 | 50 | 0 | 7.8 |
| | 125 | 12.5 | 6 | 7.0[3] |
| Placebo | 0.1 ml | — | 0 | 6.2 |

[1]determined at 15 days
[2]tested under the same conditions as agents A, B and C but not at the same time.
[3]values not statistically different from that of placebo-treated animals (P greater than or equal to 0.05)

Treatment of mice with A at 12.5 mg/kg/day resulted in 40% survival and an average survival time of 10.7 days. The relative potency of A to B was 5.3, which was statistically significant. The relative potency of A to C was 2.3, which was not statistically significant. Relative potencies were calculated by parallel line analysis.

EXAMPLE 16

Oral Treatment of Herpes Simplex Virus Infection in Mice

Twenty gram ICR/Ha mice were injected intraperitoneally (i.p.) with 0.5 ml of a $10^{-5}$ dilution of a stock preparation of Herpes simplex virus type 1 (HSV-1), strain Schooler. This virus challenge infected each animal with approximately 50 to 100 LD$_{50}$s. Starting immediately after virus infection and continuing twice daily for 7 days, each animal was treated by oral gavage in groups of 10 with: 250 μg, 125 μg, 8 μg or 2 μg of (S)-9-(2,3-dihydroxy-1-propoxymethyl)guanine; 500 μg, 125 μg, 31 μg, 8 μg or 2 μg of racemic 9-(2,3-dihydroxy-1-propoxymethyl)guanine; or placebo (physiological saline, pH 11.5). All compounds were solubilized in physiological saline, pH 11.5. The mice were observed daily for 15 days at the same time each day and the day of death was recorded for each animal.

The statistical analyses were carried out as described in Example 15.

| Oral Treatment of Intraperitoneal HSV-1 Infection of Mice | | | | |
|---|---|---|---|---|
| Chemical Agent | Animal Treatment | | Percent Survival[1] | Avg. Survival Time (Days) |
| | μg/dose | mg/kg/day | | |
| (S)—9-(2,3-dihydroxy-1-propoxymethyl)guanine | 250 | 25 | 10 | 9.8 |
| | 125 | 12.5 | 20 | 10.2 |
| | 31 | 3.1 | 0 | 7.5[3] |
| | 8 | 0.8 | 0 | 7.2[3] |
| | 2 | 0.2 | 0 | 7.2[3] |
| Racemic 9-(2,3-dihydroxy-1-propoxymethyl)guanine | 500 | 50 | 20 | 10.7 |
| | 125 | 12.5 | 10 | 8.4[3] |
| | 31 | 3.1 | 0 | 7.6[3] |
| | 8 | 0.8 | 0 | 6.8[3] |
| | 2 | 0.2 | 0 | 6.9[3] |
| Acyclovir[2] | 1000 | 100 | 60 | 11.4 |
| | 500 | 50 | 20 | 8.2 |
| | 125 | 12.5 | 0 | 6.6[3] |
| | 31 | 3.1 | 0 | 6.3[3] |
| Placebo | — | — | 0 | 7.0 |

[1]determined at 15 days
[2]tested under the same conditions as the two above-listed agents but not at the same time.
[3]values not statistically different from that of placebo-treated animals (p greater than or equal to 0.05)

Conclusion (S)-9-(2,3-Dihydroxy-1-propoxymethyl)guanine used at 25 or 12.5 mg/kg/day, and racemic 9-(2,3dihydroxy propoxymethyl)guanine used at 50 mg/kg/day conferred significant protection over placebo-treated animals, as measured by average survival time.

EXAMPLE 17

Oral Treatment of Herpes Simplex Virus Infection in Mice

Twenty gram ICR/Ha mice were injected intraperitoneally (i.p.) with 0.5 ml of a $10^{-5}$ dilution of a stock preparation of Herpes Simplex virus type 1 (HSV-1), strain Schooler. This virus challenge infected mice with approximately 50 to 100 LD$_{50}$. Starting immediately after virus infection and continuing twice daily for 7 days, each animal was treated by oral gavage in groups of 10 with: 500 μg, 125 μg, 31 μg or 8 μg of (S)-9-(2,3-dihydroxy-1propoxymethyl)guanine; 500 μg, 125 μg, 31 μg or 8 μg of acyclovir or placebo (physiological saline, pH 11.5). All compounds were solubilized in physiological saline, pH 11.5. The mice were observed for 15 days at the same time each day and the day of death was recorded for each animal.

The statistical analyses were carried out as described in Example 15.

| Oral Treatment of Intraperitoneal HSV-1 Infection of Mice | | | |
|---|---|---|---|
| Chemical Agent | Animal Treatment | | Percent Survival[a] | Avg. Survival Time (Days) |
| | μg/dose | mg/kg/day | | |
| (S)—9-(2,3- dihydroxy-1- propoxymethyl) guanine | 500 | 50 | 30 | 12.9 |
| | 125 | 12.5 | 0 | 8.1 |
| | 31 | 3.1 | 0 | 6.9[b] |
| | 8 | 0.8 | 0 | 6.2[b] |
| Acyclovir | 500 | 50 | 20 | 8.7 |
| | 125 | 12.5 | 10 | 7.6 |
| | 31 | 3.1 | 0 | 6.5[b] |
| | 8 | 0.8 | 0 | 6.1[b] |
| Placebo | — | — | — | 6.0 |

[a]determined at 15 days
[b]values not statistically different from that of placebo-treated animals (p greater than or equal to 0.05)

Conclusion

Both (S)-9-(2,3-dihydroxy-1-propoxymethyl)-guanine and acyclovir used at 50 and 12.5 mg/kg/day conferred significant protection over placebo-treated animals, as measured by average survival time. The relative potency of (S)-9-(2,3-dihydroxy-1-propoxymethyl)-guanine to acyclovir was 2.8, which was statistically significant.

Following the methods set forth above in Examples 2, 5, 6, 7 and 13, a racemic mixture of each (S)-enantiomer and its corresponding (R)-enantiomer was prepared.

Set forth below is the name of each racemic compound prepared together with the relevant physical data:

9-(2,3-Diacetoxy-1-propoxymethyl)guanine (racemate of compound of Example 2)

A slightly off-white powder (yield 62%), m.p. 222.5°–224° C. Structure and purity were confirmed by NMR and TLC (9:1 CHCl$_3$-MeOH). Anal. calcd. for C$_{13}$H$_{17}$N$_5$O$_6$:
C, 46.01; H, 5.05; N, 20.64.

Found: C, 45.64; H, 4.97; N, 20.37.

9-(2,3-Dioctanoyloxy-1-propoxymethyl)guanine (racemate of compound of Example 5)

A white solid (yield 39%) which softened above 145° C. and was shown to be of good purity by NMR and TLC (9:1 CHCl$_3$-MeOH).
Anal. calcd. for 94% (C$_{25}$H$_{41}$N$_5$O$_6$. H$_2$O)+6% inorganic silica gel:
C, 53.69; H, 7.75; N, 12.53
Found: C, 53.77; H, 7.59; N, 12.52.

9-(2,3-Dibenzoyloxy-1-propoxymethyl)guanine (racemate of compound of Example 6)

An amorphous white solid which softened at above 70° C. Structure and purity were confirmed by NMR, TLC (9:1 CHCl$_3$-MeOH) and mass spectrum.
Anal. calcd. for 90% (C$_{23}$H$_{21}$N$_5$O$_6$.2H$_2$O)+10% inorganic silica gel:
C, 49.77; H, 4.54; N, 12.62.
Found: C, 49.76; H, 4.58; N, 12.55.

9-[2,3-Bis(phenoxyacetoxy)-1-propoxymethyl]guanine (racemate of compound of Example 7)

A white solid, with m.p. 95–100° C. The material was judged to have good purity by NMR and TLC (9:1 CHCl$_3$-MeOH).
Anal. calcd. for 93.6% (C$_{25}$H$_{25}$N$_5$O$_8$.0.75-H$_2$O)+6.4% inorganic silica gel:
C, 52.31; H, 4.65; N, 12.20.
Found: C, 52.53; H, 4.66; N, 12.05.

9-(2,3-Dihydroxy-1-propoxymethyl)guanine cyclic carbonate, alternatively named as 9-(2-oxo-1,3-dioxolan-4-yl-methoxymethyl)guanine (racemate of compound of Example 13)

A white solid (yield 49%) which upon recrystallization from water gave white crystals, m.p. 208°–211° C. Structure and purity were confirmed by NMR and TLC (80:20:2 CHCl$_3$-MeOH-H$_2$O).
Anal. calcd. for 96.5% (C$_{10}$H$_{11}$N$_5$O$_5$.H$_2$O)+3.5% inorganic silica gel:
C, 38.73; H, 4.22; N, 22.59.
Found: C, 39.03; H, 4.02; N, 22.31.
What is claimed is:
1. A compound of formula:

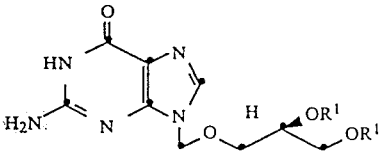

wherein each R$^1$ is independently H or

where each R$^2$ is independently alkyl of 1 to 20 carbon atoms which may be straight chain or branched, saturated or mono- or polyunsaturated, and may contain one or more hydroxy, amino, or carboxyl groups, phenyl, phenyl substituted with halogen, phenyl substituted with alkyl of 1 to 4 carbon atoms, phenyl substituted with alkyl of 1 to 4 carbon atoms, pyridyl, piperidyl, furyl, imidazolyl, tetrahydrofuryl, thienyl, phenylalkyl wherein the alkyl moiety has 1 to 4 carbon atoms, alkoxyalkyl wherein both the alkoxy and alkyl moieties contain 1 to 4 carbon atoms, or phenoxy substituted with alkyl having 1 to 4 carbon atoms, or the two R¹ groups together are

2. A compound according to claim 1, wherein R² contains an amino group.

3. A compound according to claim 1, wherein R² contains an hydroxy group.

4. A compound according to claim 1, wherein R² contains a carboxyl group.

5. A compound according to claim 1, wherein R² is —CH(CH₃)NH₂, —CH₂NH₂, —CH(CH₂OH)NH₂, —(CH₂)₂COOH, —CH₂OH, or —CH(NH₂)CH₂COOH.

6. A compound of claim 1 wherein each R is H.

7. A compound according to claim 1, wherein said pharmaceutically acceptable cation is sodium, potassium, ammonium, C₁ to C₄ alkyl substituted ammonium, magnesium/2, calcium/2, or aluminum/3.

8. A compound of claim 1 having the name (S)-9-(2,3-dihydroxy-1-propoxymethyl)guanine.

9. A compound of claim 1 having the name either (S)-9-(2,3-dibenzyloxy-1-propoxymethyl)guanine or alternatively 9-(2,3-di-O-benzyl-L-glycer-1-yloxymethyl)guanine.

10. A composition comprising the compound of claim 1 in an anti-viral effective amount in combination with a pharmaceutically acceptable carrier.

11. A method of treating a herpes virus infection in a mammalian or avian or piscine species comprising administering a compound of claim 1 in a quantity effective to impart an anti-herpes virus effect.

12. A compound of the formula:

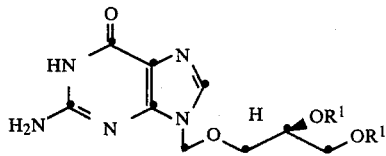

wherein each R¹ is independently H or benzyl or

wherein each R² is independently alkyl of 1 to 20 carbon atoms which may be straight chain or branched, saturated or mono- or polyunsaturated, and ay contain one or more hydroxy, amino or carboxyl groups, with the proviso that if R¹ is H or

then a hydrogen on each hydroxy and carboxy group of R² is replaced by a benzyl group and a hydrogen of each amino group of R² is replaced with a carbobenzyloxy group.

* * * * *